(12) United States Patent
Wahrenberg

(10) Patent No.: US 11,259,782 B2
(45) Date of Patent: Mar. 1, 2022

(54) MEDICAL IMAGING DATA PROCESSING APPARATUS AND METHOD

(71) Applicant: Toshiba Medical Systems Corporation, Otawara (JP)

(72) Inventor: Magnus Wahrenberg, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 1205 days.

(21) Appl. No.: 15/627,944

(22) Filed: Jun. 20, 2017

(65) Prior Publication Data

US 2018/0360425 A1    Dec. 20, 2018

(51) Int. Cl.
| | | |
|---|---|---|
| *A61B 8/08* | (2006.01) | |
| *G06T 7/00* | (2017.01) | |
| *A61B 8/00* | (2006.01) | |
| *G06T 15/50* | (2011.01) | |
| *G06T 15/00* | (2011.01) | |

(52) U.S. Cl.
CPC .............. *A61B 8/5207* (2013.01); *A61B 8/08* (2013.01); *A61B 8/44* (2013.01); *A61B 8/461* (2013.01); *A61B 8/466* (2013.01); *A61B 8/483* (2013.01); *G06T 7/0012* (2013.01); *G06T 15/005* (2013.01); *G06T 15/506* (2013.01); *A61B 8/0866* (2013.01); *G06T 2210/41* (2013.01)

(58) Field of Classification Search
CPC ........... A61B 8/5207; A61B 8/08; A61B 8/44; A61B 8/461; A61B 8/466; A61B 8/483; G06T 7/0012; G06T 15/005; G06T 15/506
See application file for complete search history.

(56) References Cited

U.S. PATENT DOCUMENTS

| | | |
|---|---|---|
| 9,384,548 B1 | 7/2016 | Wahrenberg |
| 9,468,420 B2 | 10/2016 | Wahrenberg |
| 2013/0265302 A1 | 10/2013 | Olivan Bescos |
| 2016/0038124 A1 | 2/2016 | Tsujita |
| 2016/0242740 A1 | 8/2016 | Day |

OTHER PUBLICATIONS

Gordon Kindlmann, et al. "Curvature-Based Transfer Functions for Direct Volume Rendering: Methods and Applications", VIS '03 Proceedings of the 14$^{th}$ IEEE Visualization, 2003, 8 pages.
Yubo Zhang, et al. "Lighting Design for Globally Illuminated Volume Rendering", IEEE Trans Vis Comput Graph, 2013, 10 pages.

*Primary Examiner* — Amelie R Davis
*Assistant Examiner* — Marjan Saboktakin
(74) *Attorney, Agent, or Firm* — Oblon, McClelland, Maier & Neustadt, L.L.P.

(57) ABSTRACT

A medical image processing apparatus comprises processing circuitry configured to: obtain a medical imaging data set representative of at least part of at least one surface; render from the medical imaging data set at least one image of the at least part of the at least one surface, wherein the or each image is rendered using a respective lighting configuration; and determine a measure of lighting quality for the or each rendered image; wherein, for the or each rendered image, the determining of the measure of lighting quality comprises, for each of a plurality of locations on the at least part of the at least one surface, determine a correspondence between a curvature of the at least one surface at that location and a lighting value at that location, wherein the lighting value is obtained from the rendering of the image; and determine the measure of lighting quality based on the determined correspondences.

15 Claims, 7 Drawing Sheets

MEDICAL IMAGING DATA PROCESSING APPARATUS AND METHOD

FIELD

Embodiments described herein relate generally to a method of, and apparatus for, obtaining a measure of lighting quality for an image rendered from medical imaging data, where the measure of lighting quality is based on curvature.

BACKGROUND

It is known to render three-dimensional (3D) imaging data to produce a rendered image that appears to be three-dimensional. In four-dimensional (4D) imaging systems, a series of three-dimensional images obtained at different times may be dynamically rendered to produce a moving 3D image, for example a 3D ultrasound movie.

Lighting effects may be added to a 3D or 4D image such that a subject of the image appears to be illuminated from a given position and/or direction. In recent years, 3D and 4D medical images have been made more realistic through the use of advanced lighting techniques (referred to as global illumination, gradient free lighting, subsurface scattering or photon mapping) that simulate illumination with a more physically accurate model than was previously used.

Global illumination (GI) is gaining in popularity and may be considered to be ubiquitous in ultrasound. Global illumination may previously have been considered to occupy a niche in obstetrics, but now is used in a wide range of applications, for example cardiac, radiology or vascular imaging, for example three-dimensional Doppler imaging. There is also interest in the use of global illumination in other modalities, for example CT (computed tomography) and MR (magnetic resonance) imaging.

Global illumination may require the use of more parameters than are used in traditional rendering. Parameters used in global illumination may include, for example, light position, color map, brightness and radiosity parameters. An image may be rendered using multiple virtual light sources, each of which may have associated parameters including, for example, position, direction, intensity and/or color.

A user may want to use many different GI parameters in order to create high quality images. However, it has been shown by evaluations with clinicians that even a simple parameter (for example, light direction) may be difficult for the user to manage. This may especially be the case when complex scenes are rendered. The global nature of the visualization method may mean that parameters that are easy to understand in concept may be difficult to manage.

Light direction may have a large impact on perceived image quality. FIG. 1 shows a set of nine images in which a set of medical image data, which in this case is representative of a fetal face, is rendered using different light directions. The images are arranged by light direction. For example, the top left image is illuminated by light shining from the top left and the bottom right image is illuminated by light shining from the bottom right.

Some light directions may result in a lack of contrast in the image. For example, in the central image of FIG. 1, the fetal face is illuminated as if by a light shining directly at the fetal face from the direction of the viewer. As a result, few shadows are visible in the image. It may be more difficult to distinguish features such as eyes, nose and mouth in an image with straight-on lighting than in an image in which the light is incident at an angle relative to the viewing direction.

Other light directions may result in excessive shadowing, which may obscure parts of the image that are in shadow.

In some circumstances, the context of a medical scan (for example, which anatomical features are being imaged) may not be known by an imaging system. The context of the medical scan may be ever changing, for example in the case of a live modality such as ultrasound. In obstetrics, a scan may contain hands, legs, and spine in addition to the face of the fetus.

BRIEF DESCRIPTION OF THE DRAWINGS

Embodiments are now described, by way of non-limiting example, and are illustrated in the following figures, in which:—

DETAILED DESCRIPTION

Figure 1:
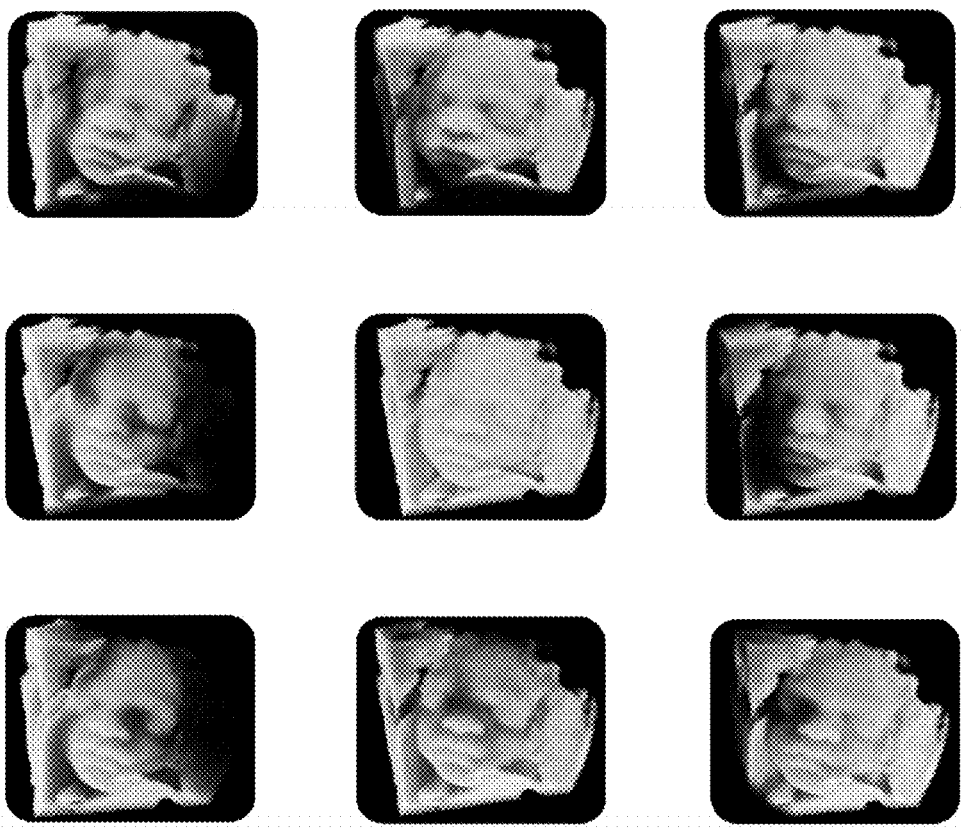
FIG. 1 shows a plurality of rendered images of a set of medical imaging data that is representative of a fetal face.

Certain embodiments provide a medical image processing apparatus comprising processing circuitry configured to: obtain a medical imaging data set representative of at least part of at least one surface; render from the medical imaging data set at least one image of the at least part of the at least one surface, wherein the or each image is rendered using a respective lighting configuration; and determine a measure of lighting quality for the or each rendered image; wherein, for the or each rendered image, the determining of the measure of lighting quality comprises: for each of a plurality of locations on the at least part of the at least one surface, determining a correspondence between a curvature of the at least one surface at that location and a lighting value at that location, wherein the lighting value is obtained from the rendering of the image; and determining the measure of lighting quality based on the determined correspondences.

Certain embodiments provide a medical image processing apparatus comprising processing circuitry configured to: obtain a sequence of medical imaging data sets, each representative of at least part of at least one surface; and for each of the sequence of medical imaging data sets: render from the medical imaging data set at least one image of the at least part of the at least one surface, wherein the or each image is rendered using a respective lighting configuration; and determine a measure of lighting quality for the or each rendered image; wherein, for the or each rendered image, the determining of the measure of lighting quality comprises: for each of a plurality of locations on the at least part of the at least one surface, determining a correspondence between a curvature of the at least one surface at that location and a lighting value at that location, wherein the lighting value is obtained from the rendering of the image; and determining the measure of lighting quality based on the determined correspondences; and wherein the measure of lighting quality is dependent on a comparison of a lighting configuration with which the medical image data set is rendered and at least one lighting configuration with which at least one preceding medical image data set in the sequence is rendered, such that more similar lighting configurations result in a better measure of lighting quality.

Certain embodiments provide a medical image processing apparatus comprising processing circuitry configured to determine a mapping of curvature values to desired lighting values by: obtaining image data corresponding to at least one image selected by at least one user; processing the image data to obtain, for each of a plurality of locations in the image data, a respective curvature value and a respective lighting value; and for each of the obtained curvature values, using the obtained lighting values for locations having that curvature value to determine a desired lighting value for that curvature value.

Certain embodiments provide a method comprising obtaining a medical imaging data set representative of at least part of at least one surface; rendering from the medical imaging data set at least one image of the at least part of the at least one surface, wherein the or each image is rendered using a respective lighting configuration; and determining a measure of lighting quality for the or each rendered image; wherein, for the or each rendered image, the determining of the measure of lighting quality comprises: for each of a plurality of locations on the at least part of the at least one surface, determining a correspondence between a curvature of the at least one surface at that location and a lighting value at that location, wherein the lighting value is obtained from the rendering of the image; and determining the measure of lighting quality based on the determined correspondences.

Figure 2:
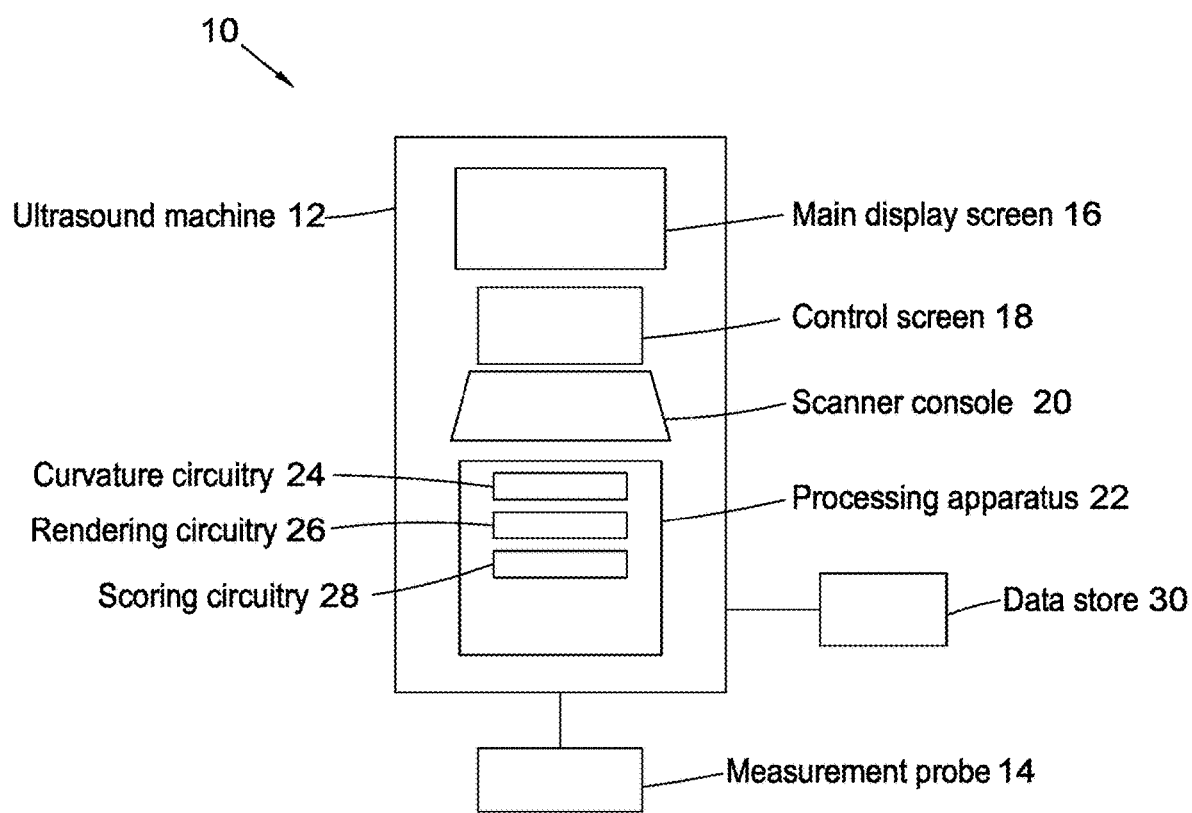
FIG. 2 is a schematic diagram of a medical imaging apparatus in accordance with an embodiment.

A medical imaging apparatus 10 according to an embodiment is shown in FIG. 2. The medical imaging apparatus 10 comprises an ultrasound machine 12 and associated measurement probe 14. Any suitable type of ultrasound machine 12 and measurement probe 14 may be used, for example any ultrasound machine 12 and measurement probe 14 that are configured to obtain ultrasound image data that is suitable for 3D or 4D imaging. In the present embodiment, the ultrasound machine 12 and measurement probe 14 are configured to obtain three- or four-dimensional ultrasound data in real-time or near-real-time.

The ultrasound machine 12 and measurement probe 14 are configured to acquire ultrasound data that is representative of at least part of at least one surface of at least one anatomical feature of a patient or other subject. The at least one anatomical feature may comprise, for example, at least one organ or bone. The at least one anatomical feature may comprise at least one pathological feature, for example a tumor. The at least one anatomical feature may comprise at least one artificial feature, for example a stent or implant. The at least one anatomical feature may be at least one anatomical feature of a fetus in the womb.

The at least one surface may comprise any appropriate boundary of an anatomical feature, for example an outer boundary of an organ, tumor or fetus. The at least one surface may comprise a boundary between two anatomical features, or between two parts of a single anatomical feature. The at least one surface may be internal to the patient or other surface.

In other embodiments the medical imaging apparatus 10 may comprise an apparatus of any imaging modality that is configured to provide three- or four-dimensional medical imaging data, for example a CT (computed tomography) scanner, an MRI (magnetic resonance imaging) scanner, an X-ray scanner, a PET (positron emission tomography) scanner, or a SPECT (single photon emission computed tomography) scanner. The three- or four-dimensional medical imaging data may be obtained by combining multiple two-dimensional scans.

The ultrasound machine 12 comprises a main display screen 16 for displaying a main ultrasound image, a control screen 18 for displaying control information, and a scanner console 20. In this embodiment, the scanner console 20 comprises an input device or devices such as input buttons or knobs, a computer keyboard, a mouse or a trackball. In alternative embodiments, the control screen 18 is a touch screen, which is both a display device and a user input device. Further embodiments may comprise a control screen 18, display screen or main display screen 16 that does not form part of the ultrasound machine 12. The ultrasound machine 12 also comprises a data store 30 for storing volumetric image data.

The ultrasound machine 12 comprises a processing apparatus 22 for processing of data, including image data. The processing apparatus 22 provides a processing resource for automatically or semi-automatically processing imaging data sets. The processing apparatus 22 comprises a central processing unit (CPU) and Graphical Processing Unit (GPU).

In the present embodiment, the processing apparatus 22 includes curvature circuitry 24 configured to determine curvatures from ultrasound data, rendering circuitry 26 configured to render ultrasound data, and scoring circuitry 28 configured to obtain a measure of lighting quality. The curvature circuitry 24, rendering circuitry 26 and scoring circuitry 28 may each be implemented in the CPU, in the GPU, or in a combination of the CPU and the GPU.

In alternative embodiments, the processing apparatus 22 comprising the curvature circuitry 24, rendering circuitry 26 and scoring circuitry 28 may be part of any suitable medical imaging apparatus (for example, a CT scanner or MR scanner) or image processing apparatus (for example, a PC or workstation). The processing apparatus 22 may be configured to process any appropriate modality of volumetric image data, for example ultrasound, CT, MR, X-ray, PET or SPECT data.

In the present embodiment, the processing apparatus 22 is configured for real-time or near-real time processing of ultrasound data. In other embodiments, the processing apparatus 22 is configured to process stored ultrasound data, for example data stored in data store 30, or in a remote data store (not shown) which may form part of a Picture Archiving and Communication System (PACS). The data store 30 or remote data store may comprise any suitable form of memory storage.

In the present embodiment, the curvature circuitry 24, rendering circuitry 26 and scoring circuitry 28 are each implemented in the CPU and/or GPU of processing apparatus 22 by means of a computer program having computer-readable instructions that are executable to perform the method of the embodiment. However, in other embodiments each of the curvature circuitry 24, rendering circuitry 26 and scoring circuitry 28 may be implemented in software, hardware or any suitable combination of hardware and software. In some embodiments, the various circuitries may be implemented as one or more ASICs (application specific integrated circuits) or FPGAs (field programmable gate arrays).

The processing apparatus 22 also includes a hard drive and other components including RAM, ROM, a data bus, an operating system including various device drivers, and hardware devices including a graphics card. Such components are not shown in FIG. 2 for clarity.

In the present embodiment, a single apparatus (medical imaging apparatus 10) is configured to acquire medical image data, to render images from the medical image data, and to process the images to obtain a measure of lighting quality. In other embodiments, a different apparatus may be used to render and/or process the images than is used to acquire the medical image data. For example, the curvature circuitry 24, rendering circuitry 26 and scoring circuitry 28 may be implemented in a processing apparatus that is not part of an ultrasound machine 12 or other imaging apparatus.

Figure 3:
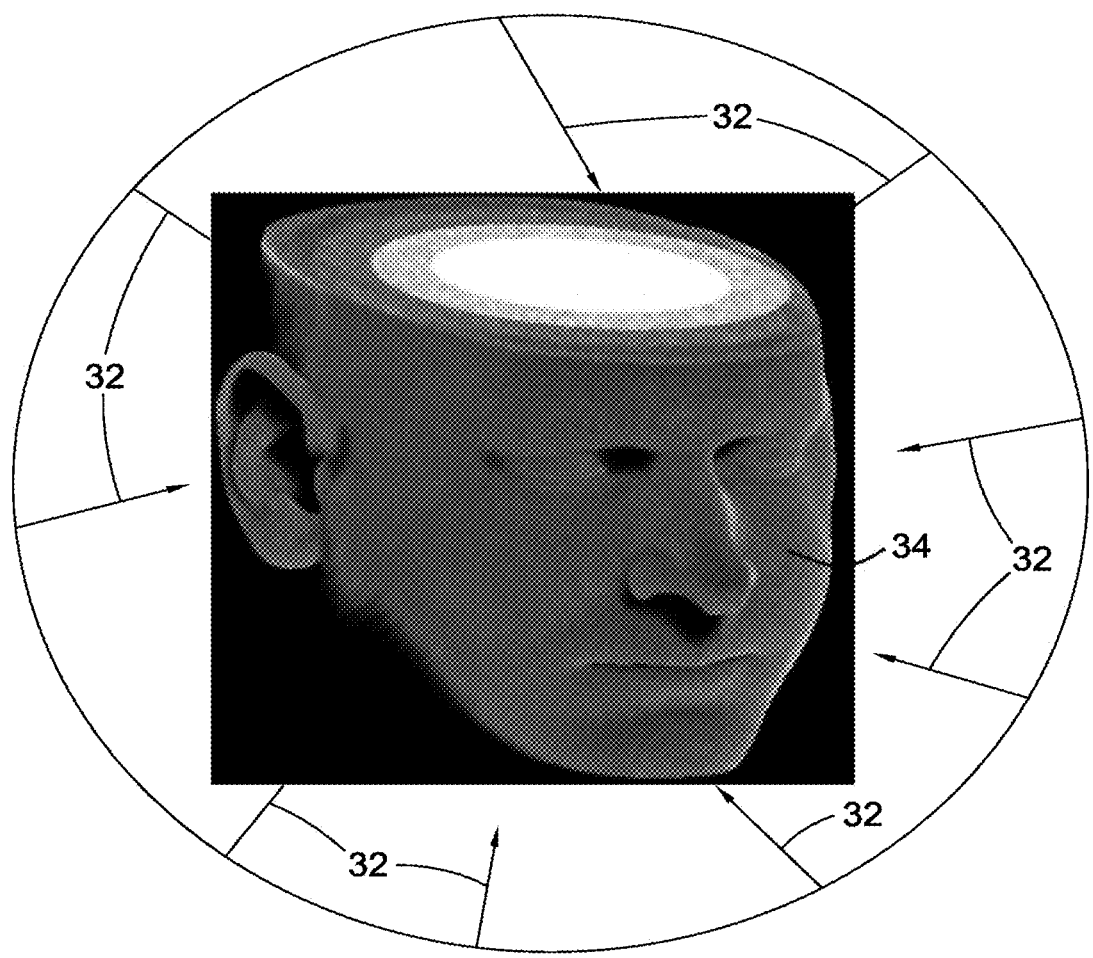
FIG. 3 is a schematic illustration of a face being illuminated from multiple light directions.

As described above, it may be difficult for a user to determine which light direction to use in rendering, especially when using more advanced illumination methods such as global illumination. FIG. 3 shows a plurality of light directions (shown as arrows 32) relative to a face 34. Different light directions may result in different lighting effects, for example as shown in FIG. 1.

Figure 4:
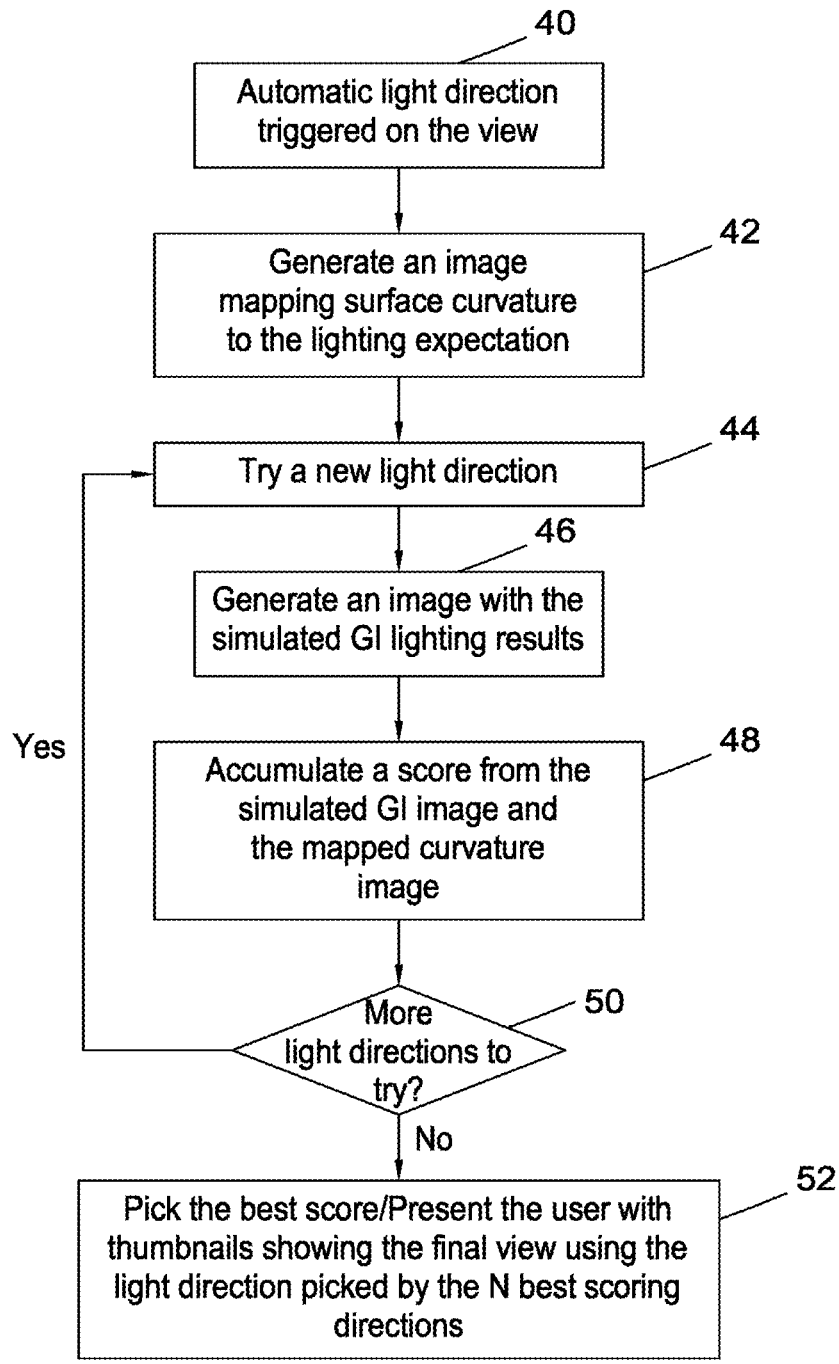
FIG. 4 is a flow chart illustrating in overview a method of obtaining lighting scores for multiple light directions in accordance with an embodiment.

FIG. 4 is a flow chart illustrating in overview a method of an embodiment in which a light direction is automatically selected by determining a lighting score for each of a plurality of light directions, and selecting the light direction having the best lighting score.

Turning to the stages of FIG. 4 in detail, at stage 40 an operator scans an anatomical region of a patient or other subject using the measurement probe 14. The operator triggers a process of automatically determining an optimal light direction, which comprises stages 42 to 52 of FIG. 4. In the present embodiment, the operator triggers the process by pressing a button. In other embodiments, any suitable input method may be used.

In some embodiments, an optimal light direction is determined in real time whenever ultrasound data is being acquired. In other embodiments, a light direction determination mode may be toggled on and off.

The anatomical region comprises at least one anatomical feature. The ultrasound machine 12 processes the data received from the measurement probe 14 to obtain a volumetric medical imaging data set which is representative of at least part of at least one surface of the at least one anatomical feature. The volumetric data set comprises a plurality of voxels, each voxel having an associated position in the three-dimensional space of the volumetric data set and an associated intensity.

In the present embodiment, the anatomical region that is scanned is the patient's womb, and the volumetric data set is representative of at least part of the surface of a fetus, in particular the fetal face. In other embodiments, the volumetric data set may be representative of any surface or surfaces of any anatomical feature or features. The volumetric data set may comprise data acquired using any appropriate imaging modality.

The curvature circuitry 24 receives the volumetric data set. In the present embodiment, the curvature circuitry 24 also receives information about a view to be rendered, including a viewing direction. The information about the view to be rendered may be obtained in any suitable way. For example, the information about the view to be rendered may be provided by a user. For example, operator may press the button to initiate the determining of light direction after they have chosen a suitable view.

Figure 5:
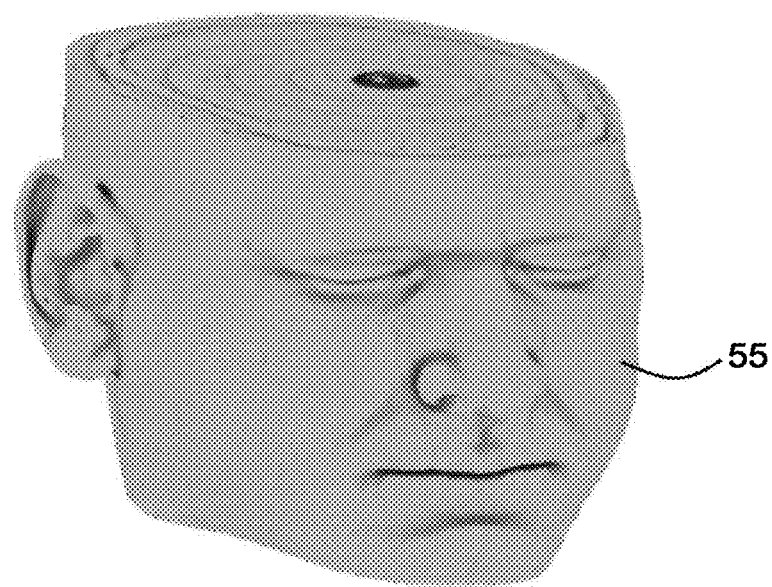
FIG. 5 is an illustration of an image in which certain surface features have been extracted by a curvature transfer function.

At stage 42, the curvature circuitry 24 generates a curvature image from the volumetric data set. FIG. 5 shows an example of a curvature image of a face 55. The greyscale value at each location on the surface of the face is dependent on a curvature value at that location.

One method of obtaining the curvature image 55 is described below. In other embodiments, any method may be used in which a curvature value is determined for each of a plurality of locations on at least part of at least one surface, and at each of the plurality of locations a lighting level is allocated based on the determined curvature value.

In the present embodiment, the curvature circuitry 24 casts a plurality of rays from the viewing direction towards the surface of the fetal face. Each ray samples the volumetric data set at a number of sampling points. When the ray reaches a sampling point whose intensity value indicates that the ray has reached the surface of the imaged structure (in this embodiment, the fetal face) the ray terminates, and the curvature circuitry 24 records the position and intensity value of that sampling point (which may be called the ray termination point). The positions of the ray termination points may be considered to form an isosurface representative of the surface of the imaged structure.

For each ray, the curvature circuitry 24 calculates a curvature value (k1, k2) at the ray termination point.

Curvature may represent a change of a normal vector of the surface, for example the change of the normal vector in three dimensions. In general, curvature at a point can comprise curvature in two principal planes, each of which is perpendicular to the gradient of the surface at that point. The two principal planes are orthogonal to each other. The curvature at a given point on the surface may be represented by a curvature value comprising two curvature numbers (k1, k2), one for each principal plane.

The ray termination point may be described as being a point of intersection with an isosurface that represents the imaged structure. The curvature may represent the change of the normal vector, for example the change of the normal vector in three dimensions. For each ray termination point, the region around the ray termination point may be sampled to obtain a gradient and second derivative (for example, Hessian) of the isosurface at that point. The gradient and second derivative may then be used to derive the curvature at that point.

At each ray termination point, the curvature circuitry 24 allocates a lighting value to that ray termination point based on the determined curvature value (Id, k2) at that ray termination point. In the present embodiment, the lighting values are allocated using a 2D transfer function that maps each curvature value (k1, k2) to a respective lighting value (for example, greyscale value). The 2D transfer function may be referred to as a curvature transfer function.

In other embodiments, any mapping from curvature value (k1, k2) to lighting value may be used, for example any transfer function or lookup table.

In the present embodiment, lighting value is dependent on both k1 and k2. In other embodiments, lighting value may be dependent on only one of k1 and k2, or on any suitable parameter derived from k1 and k2 (for example, for example a maximum or minimum principal curvature).

In the present embodiment, the allocation of lighting values in dependence on curvature follows the following principles. Cavities should be shaded. Creases should be shaded. Raised features should be well lit. Less curved features should not skew the results.

Cavities may be considered to be regions in which curvature is negative in both principal planes (both k1 and k2 are negative). The curvature circuitry 24 may allocate lighting values such that if k1 and k2 are both strongly negative at a point, the lighting value allocated to that point may be very dark. Cavities having a more strongly negative curvature value may be allocated a darker lighting value than those with a less negative curvature value.

Creases may be considered to be regions in which curvature is negative in one principal plane and is not negative, or is only slightly negative, in the other principal plane. In some embodiments, if only one of k1 and k2 is strongly negative, the curvature circuitry 24 allocates a lighting value that is less dark than if both k1 and k2 are strongly negative.

Raised features may be regions in which curvature is positive in both principal planes. If at least one of k1 and k2 is positive, the lighting value allocated may be brighter than if one or both of k1 and k2 is negative.

Less curved features may be regions in which curvature is neither strongly positive nor strongly negative. Less curved features may be allocated a lighting value that is neither particularly dark nor particularly bright.

By allocating lighting values in this way, cavities and creases may be represented as dark while raised areas are represented as bright.

It may be seen in the curvature image 55 of FIG. 5 that cavities, for example those in the ear, are darker than other parts of the image. Creases, for example around the nose and between the lips, are also darker. Lighting levels in the curvature image 55 depend only on curvature, and no lighting effects are applied.

We note that, although a curvature image 55 is shown as a rendered image in FIG. 5, the curvature image 55 is not displayed by the ultrasound machine 12 in the process of FIG. 4. The generation of the curvature image 55 comprises the determining of data corresponding to the curvature image 55 by the curvature circuitry 24. The data is determined internally without the curvature image 55 being displayed to the user.

The 2D transfer function (or, in other embodiments, any appropriate mapping of curvature value to lighting value) is configured to allocate lighting values that are considered to be desirable. The allocated lighting values may be referred to as expected or desired lighting values or lighting levels. The set of allocated lighting values may be described as a lighting expectation. The allocated lighting values may be lighting values that are expected to provide good image quality, for example good visibility of structural features such as cavities and creases.

It may be the case that different users may prefer different mappings of curvature to lighting value. For example, some users may prefer cavities and/or creases to be more strongly emphasized. Some users may prefer an image that is lighter overall than an image preferred by other users. Different mappings may look better on different display screens. Therefore, in some embodiments a user may choose between different 2D transfer functions or other mappings. The curvature circuitry 24 may use a mapping function that is preferred by an individual user or group of users. The curvature circuitry 24 may use a mapping that is trained to the preferences of an individual user. The creation of such a mapping is described below with reference to FIG. 8. The curvature circuitry 24 may select a mapping in dependence on the volumetric data set to be rendered, for example in dependence on a modality of the volumetric data set and/or in dependence on an anatomical feature that is to be rendered.

Turning again to FIG. 4, at stage 44 the rendering circuitry 26 receives the volumetric data set and the information about the view to be rendered, including the viewing direction. The rendering circuitry 26 selects a first light direction. Any suitable method of determining a first light direction may be used. For example, the rendering circuitry 26 may select a first light direction from a list. The rendering circuitry 26 may select a light direction that is at a predetermined angle with respect to the viewing direction.

In the present embodiment, only one virtual light source (referred to below as a light) is used for illumination. The curvature circuitry 24 determines a first light direction for the light, but does not determine any further positional parameters (for example, x, y, or z coordinates) for the light. The light may be considered to be positioned far enough from the surface or surfaces being rendered that x, y, z coordinates do not affect the resulting illumination.

In further embodiments, the curvature circuitry 24 may determine a first x, y and/or z position for the light. In some embodiments, the curvature circuitry 24 may determine further parameters for the light, for example intensity, color and/or directionality.

In further embodiments, multiple lights are used for illumination. The curvature circuitry 24 may determine any suitable parameters (for example, position, direction, intensity, color and/or directionality) for each of the lights.

At stage 46, the rendering circuitry 26 renders an image from the volumetric data set using the viewing direction and the light direction. In the present embodiment, the image rendered by the rendering circuitry 26 at stage 46 is not displayed to the user and is only used internally. The rendered image may be referred to as a simulated image.

In the present embodiment, the image is rendered using global illumination. The global illumination rendering uses a lighting model that includes both direct illumination by light coming directly from the light source and indirect illumination, for example illumination by light that has been scattered from another surface. In other embodiments, any suitable rendering method may be used. In the present embodiment, parameters of the global illumination rendering are set up in such a way as to provide a greyscale output image.

Figure 6:
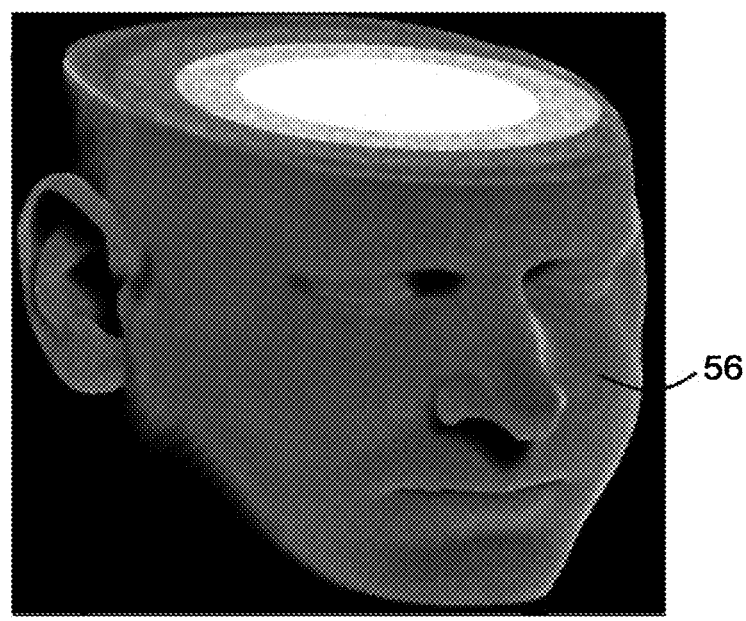
FIG. 6 is an illustration of an image depicting the amount of light energy on the surface.

As part of the rendering process, the rendering circuitry 26 determines a lighting value (which may be referred to as a local surface lighting level) for each of a plurality of points on the surface of the fetal face. The lighting value may be representative of an amount of light energy on the surface. In the present embodiment, the points for which the lighting value are determined are the same as the ray termination points used in stage 42. The ray termination points correspond to pixels of the rendered image. The lighting values are greyscale values for the pixels of the rendered image. The scene may be set up in such a way that only one isosurface is visible, or that mainly one isosurface is visible. FIG. 6 is an example of an image depicting the amount of light energy on the surface.

Depending on the position of the light source, cavities and creases in the surface may be shaded in the rendered image, while raised areas may be bright. However, the positioning and extent of the dark and bright areas in the rendered image may differ from the lighting values that have been determined to be desirable (and represented in the 2D transfer function). For example, some dark shadows are present in image of the face 56 of FIG. 6 that are not present in the curvature image of the face 55 of FIG. 5.

At stage 48, the scoring circuitry 28 determines a lighting score for the image that was rendered at stage 46. The lighting score may be considered to be a measure of lighting quality. The lighting score is indicative of the extent to which the lighting values of the rendered image are similar to the desired lighting values of the curvature image 55.

In the present embodiment, the scoring circuitry 28 determines for each of a plurality of locations on the surface (which in this embodiment are the ray termination points) a difference between the lighting value of the rendered image of stage 46 and the desired lighting value of the curvature image 55 of stage 42. The scoring circuitry 28 then squares each difference, and sums the squared differences to obtain a scalar value, which may be described as a lighting score.

In some embodiments, the scoring circuitry 28 weights the squared differences when summing the squared differences. The scoring circuitry 28 may weight the squared differences for some points with a higher weighting than the squared differences for other points. For example, the scoring circuitry 28 may assign a higher weighing to points that are representative of particular structural features (for example, cavities). The scoring circuitry may assign a higher weighting to points that are nearer the center of the image. By weighting the squared differences, some points may make a greater contribution to the lighting score than other points. For example, points that are considered to be more important may be given a higher weighting.

In one embodiment, the scoring circuitry assigns a weighting to points in which there is a linear falloff in the weight as a function of the Euclidean distance from the image center.

In some embodiments, the scoring circuitry defines a set of discrete regions representing different weights. For example, in one embodiment the scoring circuitry defines three concentric rectangles. Points falling within a first, inner one of the rectangles are assigned a weight of 100%. Points falling outside the first rectangle, but inside a second one of the rectangles are assigned a weight of 50%. Points falling outside the second rectangle but within the third, outer rectangle are assigned a weight of 20%. In other embodiments, differently-shaped regions and/or different weights may be used.

The lighting score obtained by summing the squared differences of the rendered image and the curvature image 55 may be considered to represent an estimated lighting quality. If an image has similar lighting values to that of the curvature image 55, it is considered to be of high quality. If an image has less similar lighting values to that of the curvature image 55, it is considered to be of lower quality.

In the present embodiment, a low value for the lighting score is representative of high estimated image quality. In other embodiments, a different measure of lighting quality may be used. Any suitable method may be used to compare the curvature image 55 and the rendered image. In some embodiments, a high value for lighting score may be representative of high estimated image quality.

In the present embodiment, a curvature image 55 is created by mapping curvature values to desired lighting values, and the curvature image 55 is compared to the rendered image which is obtained by rendering the volumetric data set using the light direction. Other embodiments may use any method of determining a correspondence between curvature values and lighting values. For example, a machine learning approach may be used. The curvature values may provide metrics around which a heuristic can be formulated. It may take a lot less time to train an algorithm based on curvature values than to distinguish good lighting directions directly, without the use of curvature values.

At stage 50, the curvature circuitry 24 determines whether there are other light directions to try. If so, the process of FIG. 4 returns to stage 44 and selects a further light direction, for example by selecting a light direction from a list or by changing the initial light direction by a predetermined angle. In some embodiments, a uniform distribution of light directions may be searched in no specific order. Light directions may be restricted to those in which the light direction points at the front surface visible to the user, for example the fetal face.

At stage 46, the rendering circuitry 26 renders an image using the new light direction. At stage 48, the rendering circuitry 26 determines a lighting score for the new image as described above.

In the present embodiment, stages 44 to 50 are repeated for a predetermined number of light directions, for example the light directions shown by arrows 32 of FIG. 3. In other embodiments, stages 44 to 50 are repeated until an acceptable image is achieved, for example an image having a determined lighting score that is below a threshold value.

If at stage 50 the curvature circuitry 24 determines that all the light directions have been tried, the process of FIG. 4 proceeds to stage 52.

At stage 52, the scoring circuitry 28 compares the lighting score that was determined for each of the light directions. The scoring circuitry 28 selects the light direction having the best (in this embodiment, lowest) lighting score, and displays on the main display screen 16 the image that was rendered using the selected light direction.

In a further embodiment, at stage 52 the scoring circuitry 28 compares the lighting scores and selects a subset of the light directions based on the lighting scores. For example, the scoring circuitry 28 may select a subset of a predetermined size (for example, the four, six or nine light directions having the best lighting scores). The scoring circuitry 28 may select all light directions that have a lighting score that is better than a threshold value.

The scoring circuitry 28 displays the rendered images for each of the subset of light directions as thumbnail images on the control screen 18. The user may select one of the thumbnail images to be displayed on the main display screen 16.

In the present embodiment, the rendered image or images displayed at stage 52 are the images that were rendered at stage 46. In a further embodiment, at stage 46 images are rendered at a low resolution. When a light direction is selected based on the lighting score, a high-resolution image is rendered using that lighting direction and displayed on the main display screen 16.

In another embodiment, the scoring circuitry 28 uses the lighting scores to select a light direction that is not one of the original light directions, for example a light direction that lies between two of the light directions for which images were rendered. The scoring circuitry 28 renders a new image using the selected light direction and displays the new image on main display screen 16.

In the method described above with reference to FIG. 4, heuristics are used to map surface curvature to desired levels of illumination. The heuristics are encoded as a curvature transfer function, and accumulated into a lighting score. Using the lighting score, the light direction space may be explored to find the best score and light direction. The lighting score provides a method of quantifying the appearance of the rendered image.

The method of FIG. 4 may be used to automatically determine a light direction (or other lighting parameter) for rendering. The light direction may be obtained without input from the user. The scoring circuitry 28 may pick the light direction that scores the highest. In other embodiments, the light direction may be obtained semi-automatically. For example, the determined light direction may be a refinement of a light direction that is provided by the user, or a user may choose between several automatically determined light directions.

By automating the light direction selection, the system may be easier to use. The method of FIG. 4 may provide high quality images in real time. The user may not have to consider light direction, or may be able to choose between light directions that have already been determined to produce good images. By using a light direction that has been determined to produce a high quality image, a user (for example a clinician) may be better able to interpret the image displayed. It may be important to provide a system that is as easy to use as possible and that provides high quality images even for complex scenes.

In further embodiments, the method of FIG. 4 may be used to automate the selection of any suitable lighting parameter. For example, the method of FIG. 4 may be used to automate light location in the case of a point light.

In some circumstances, methods for automating a selection of lighting parameters may not be able to depend on anatomical context. For example, data on anatomical context may not be available. The method of FIG. 4 may not be dependent on the context of the scan. It may be used for obstetric imaging of any part of the fetus. Alternatively, it may be used for any other application in which 3D or 4D imaging is used, for example radiology or cardiac uses.

In some circumstances, it may be desirable to use the same automation of lighting parameters for radiology and for cardiac and other uses. In some embodiments, the same lighting scoring method is used for all applications and anatomies. In other embodiments, different lighting scoring methods are used for different applications and/or anatomies. For example, different lighting values may be preferred in different applications, or different weightings may be used in the scoring. Different lighting scoring methods may be used for different modalities.

In the embodiment described above in relation to FIG. 4, only one virtual light is placed (a single light direction is used). In other embodiments, a plurality of lights are placed and the method of FIG. 4 cycles through the possible combinations of the plurality of lights. Where multiple lights are used, it may be particularly useful for the lighting to be automated, since placing multiple lights may be particularly difficult for a user. In further embodiments, any light configurations may be used. For example, the method of FIG. 4 may cycle through different values for direction, location, directionality, intensity or color for one or more lights.

The method of FIG. 4 may be used to get a better initial image when using global illumination, physically based rendering, glass or other related rendering modes. The fact that the solution isn't limited to a single scene means that it may find multiple applications.

In some embodiments, the processing apparatus 22 is configured to switch between a manual light position mode and an automatic light position mode. For example, the ultrasound machine 12 (or other scanner) may have a button that switches between manual light position and automatic light position. Manual light position mode allows the user to set light position manually. Automatic light position mode sets the light position manually using the method of FIG. 4.

In some embodiments, the curvature circuitry 24 is further configured to segment the medical image data set to obtain at least one segmented region, for example to obtain segmented regions that are representative of different anatomical features. The scoring circuitry 28 may use the segmentation in determining the lighting score. The segmentation may be used to exclude unimportant areas from the score.

For example, the scoring circuitry 28 may include in the determining of the lighting score only points on the surface that have been determined to be part of a desired segmented region. The scoring circuitry 28 may exclude points from the lighting score if they are part of a different, undesired, segmented region. The scoring circuitry 28 may apply a weighting to different points in dependence on which segmented region they are in.

In the embodiment of FIG. 4, one volumetric data set is rendered using several different light directions, while the viewing direction remains the same in the different renderings.

The volumetric data set may be one frame of a sequence of frames, for example frames being obtained in real time as a 4D acquisition. In some embodiments, a light direction obtained by using the method of FIG. 4 for one frame is used for subsequent frames of the sequence of frames.

However, in 4D acquisitions we might want a light direction for each frame. In a sequence of frames, the viewing direction and/or the anatomy being viewed may change with time. Therefore in some circumstances a light direction obtained for one frame may no longer be suitable for subsequent frames. However, if a light direction were to be obtained individually for each frame without consideration of preceding frames, the light direction may be unstable. The light direction may jump about between frames. Such an instability may be distracting to a user.

Figure 7:
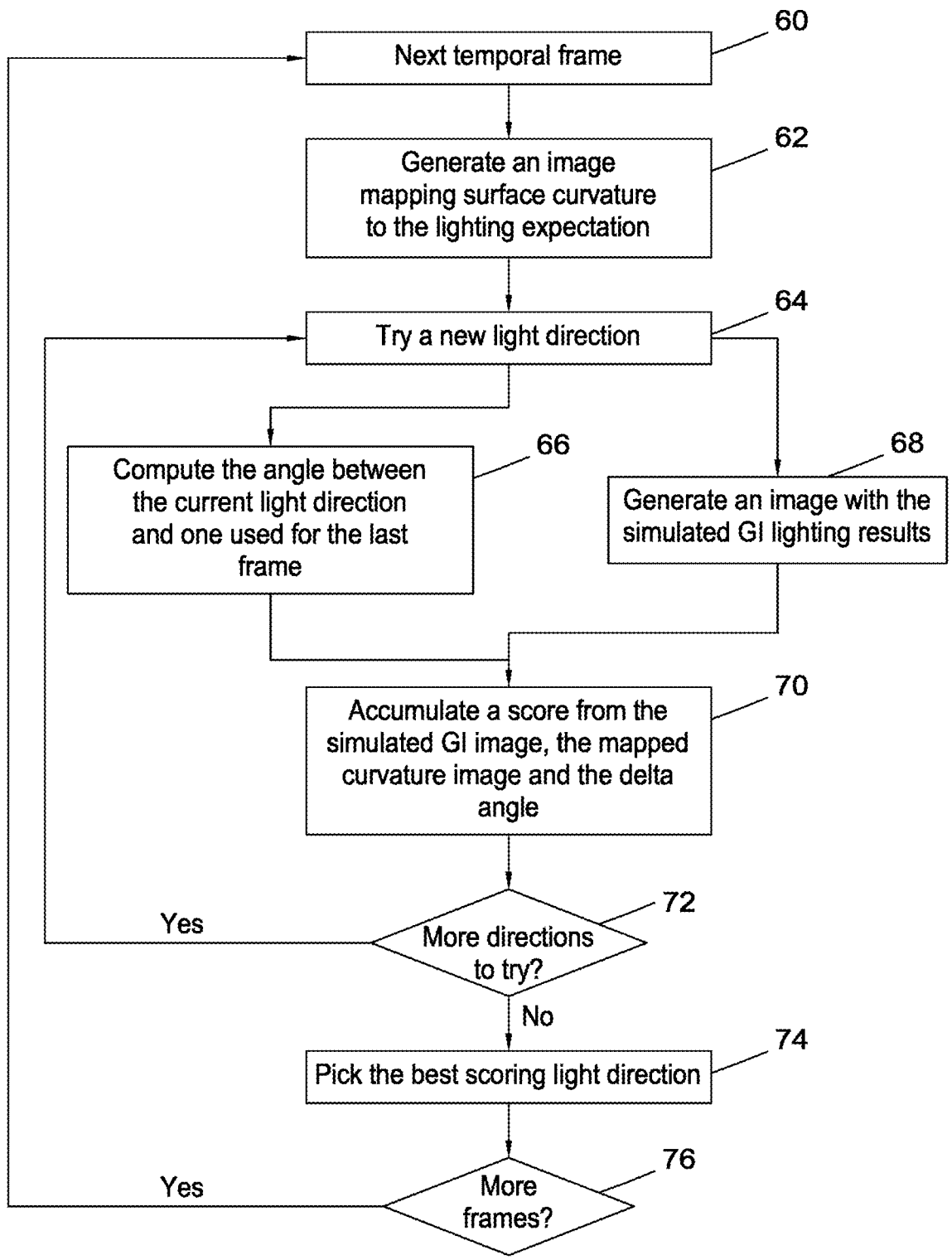
FIG. 7 is a flow chart illustrating in overview a method of selecting light directions for multiple frames of a 4D acquisition in accordance with an embodiment.

FIG. 7 is a flow chart illustrating a method in accordance with an embodiment, in which a respective light direction is obtained for each frame of a sequence of frames by adding continuity into the lighting score to avoid instability. The lighting score includes a modulation factor based on the angle between the light direction in the current frame and the light direction in the previous frame.

At a first instance of stage 60 of FIG. 7, the curvature circuitry 24 receives a volumetric data set that is representative of a first frame.

At stage 62, the curvature circuitry 24 generates a curvature image for the first frame using the method described above with reference to stage 42 of FIG. 4. At a first instance of stage 64, the rendering circuitry 26 selects a first light direction. At stage 66, the scoring circuitry 28 computes the angle between the current light direction and the light direction used for the previous frame. In the first instance of stage 66, there is no previous frame and so the angle is set to zero. At stage 68, the rendering circuitry 26 renders the volumetric data set for the first frame using the first light direction.

At stage 70, the scoring circuitry determines a lighting score for the first frame at the first light direction. The lighting score is based on summing square differences as described above with reference to stage 48 of FIG. 4, but also includes a modulation factor based on the angle between the light direction in the current frame and the light direction in the previous frame.

In the present embodiment, the lighting score is obtained by dividing the sum of square differences by the modulation factor. The modulation factor is 1 if the angle difference between the light direction in the current frame and the light direction in the previous frame is zero. The modulation factor is defined as a function which decreases as the angle difference increases. For example, the modulation factor may be an exponential function. If the angle difference is high, the lighting score increases, which is indicative of poorer lighting quality.

In some embodiments, the modulation factor may comprise a function that is anisotropic in that it modulates differently depending on whether or not the change in angle between the light direction in the current frame and the light direction in the previous frame is consistent with a previous motion of the light.

In other embodiments, any suitable modulation factor may be included in the lighting score in any suitable way. For example, the modulation factor may be added to or multiplied by any suitable parameter.

In the first instance of stage 70, the modulation factor is assigned to be 1 because there is no previous angle to be considered.

At stage 72, the curvature circuitry 24 determines whether there are more light directions to try for the first frame. In the present embodiment, the curvature circuitry 24 is configured to use a predetermined number of light directions for each frame. The process returns to stage 44. The rendering circuitry 26 selects a new light direction, generates an image for that light direction, and accumulates a lighting score for that light direction (with the modulation factor again being set to 1). Stages 64 to 72 are repeated for all the light directions for the first frame. When a lighting score has been obtained for all the light directions for the first frame, the process moves from stage 72 to stage 74. At stage 74, the scoring circuitry 28 picks the light direction having the best lighting score, and displays the rendered image of the first frame having that light direction on the main display screen 16.

The process proceeds to stage 76. At stage 76, the curvature circuitry 24 determines whether there are more frames in the sequence. If the answer is yes, the process returns to stage 60. At stage 60, the curvature circuitry 24 receives a second volumetric data set which corresponds to a second frame of the sequence.

At stage 62, the curvature circuitry 24 generates a curvature image from the second volumetric data set. At stage 64, the rendering circuitry 26 selects a first light direction for the second frame. At stage 66, the scoring circuitry 28 computes the angle between the first light direction for the second frame, and the selected light direction for the first frame (which was selected at stage 74 using the lighting scores). At stage 68, the rendering circuitry 26 renders an image from the second volumetric data set.

At stage 70, the scoring circuitry 28 determines a lighting score for the first light direction of the second frame. The lighting score includes a modulation factor based on the angle between the light direction in the second frame and the light direction in the first frame. If the light directions in the first and second frames are similar, the modulation factor is low. If the light directions in the first and second frames are less similar, the modulation factor is higher. The modulation factor is such that the lighting score is worse (in this embodiment, higher) when the light directions are dissimilar than when the light directions are similar.

In the present embodiment, the modulation factor includes the light direction in the immediately preceding frame. In other embodiments, the modulation factor may include the light directions in any suitable number of preceding frames. The modulation factor may also be dependent on whether a direction of an angle difference between successive frames is consistent with a previous direction of angle difference. In further embodiments, the modulation factor includes any appropriate lighting parameters of the lighting configuration, for example direction, location, directionality, intensity or color.

At stage 72, if there are further light directions to try, the process returns to stage 64. Stages 64 to 72 are repeated for all the predetermined light directions. Then at stage 74, the scoring circuitry 28 selects the best scoring light direction for the second frame. Because of the modulation factor in the lighting score, better scores are given to the light directions having a more similar light direction to that of the first frame. The scoring circuitry 28 displays the rendered image of the second frame having the best scoring light direction for that frame.

At stage 74, the scoring circuitry 28 picks the light direction having the best lighting score, and displays on main display screen 16 the rendered image of the first frame using that light direction.

At stage 76, the curvature circuitry 24 determines whether there are more frames in the sequence. Stages 64 to 76 are repeated until all of the frames in the sequence have been rendered.

In the present embodiment, all of the light directions in the sequence are determined automatically. In other embodiments, the light directions may also take account of user input.

By using the method of FIG. 7, light directions may be determined such that each frame is well lit, and there is continuity of lighting. The angle between the current light direction and the light direction chosen for the last frame is used to create temporal stability in the score. If the light direction appears to move between frames, it may appear to move smoothly and continuously. The method may provide good lighting even when a viewing position is changed and/or the anatomy that is viewed is changed.

The method of FIG. 7 may provide better lighting than if the same lighting configuration were used in every frame. By providing better lighting, the user may more easily interpret the images. Ease of interpretation may be particularly important when viewing a moving sequence of images in real time.

Figure 8:
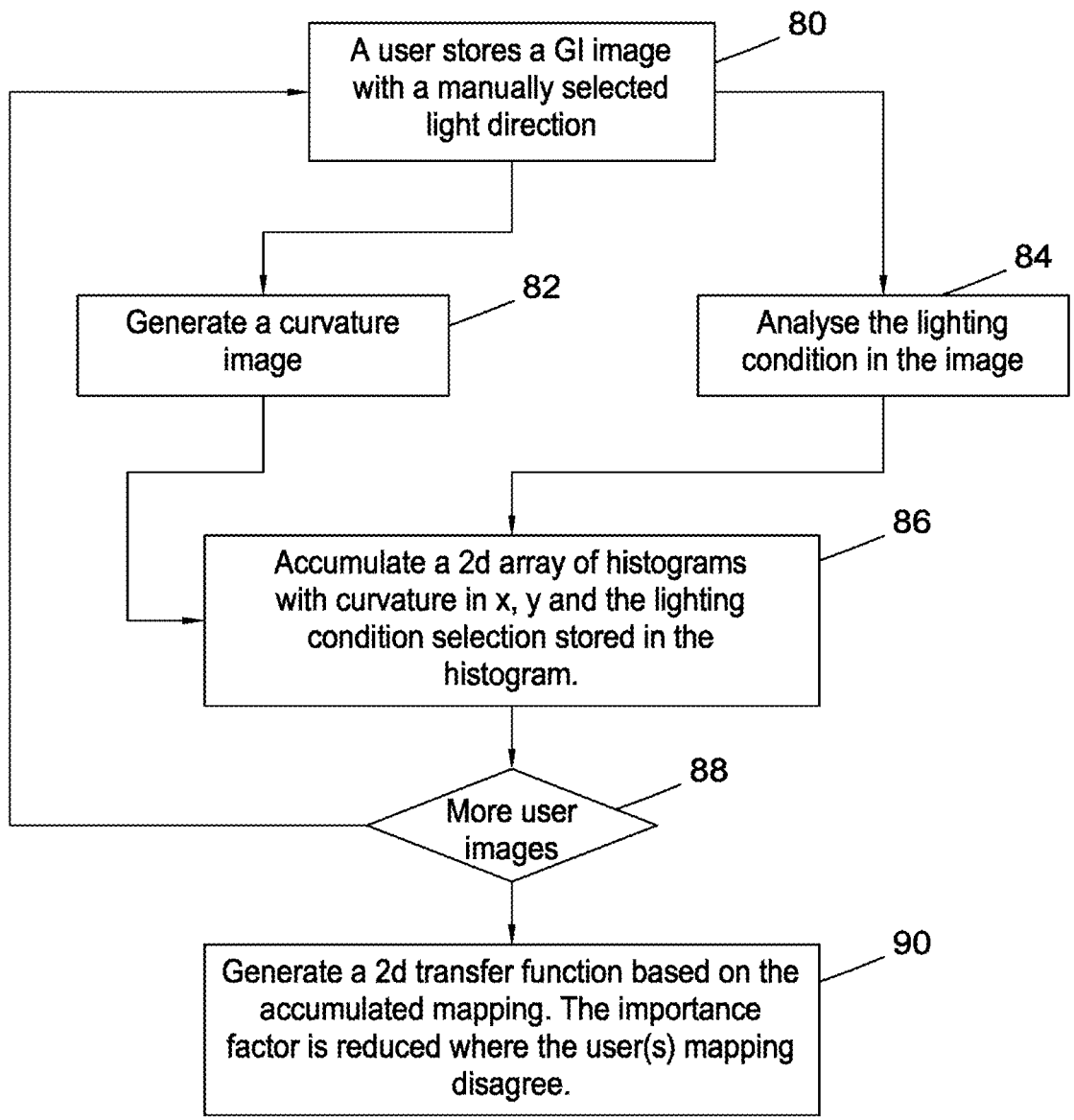
FIG. 8 is a flow chart illustrating in overview a method of generating a curvature transfer function in accordance with an embodiment.

In the embodiments above, a 2D transfer function is used to map curvature values to desired lighting values. FIG. 8 is a flow chart illustrating in overview a method of determining a 2D transfer function for mapping curvature values to desired lighting values. In other embodiments, the method of FIG. 8 may be used to determine any mapping function for mapping curvature to desired lighting value, for example to determine a lookup table.

At stage 80 of FIG. 8, a user stores an image, which in the present embodiment is a global illumination image with a manually selected light direction. In other embodiments, any suitable type of image with any suitable type of lighting may be used.

In the present embodiment, each image stored by the user is an image that has been selected by the user as having good lighting quality.

Although the present embodiment describes a user storing an image at stage 80, in other embodiments the curvature circuitry 24 may obtain image data for the image from any suitable data store at stage 80. The curvature circuitry 24 may obtain volumetric imaging data for the image, and a view direction and light direction with which the image was rendered.

At stage 82, the curvature circuitry 24 generates a curvature image from the image stored by the user. The curvature image comprises curvature values for a plurality of points on at least one surface in the image. The curvature values may be determined using any suitable method, for example as described above with reference to stage 42 of FIG. 4.

At stage 84, the curvature circuitry 24 analyses the lighting condition in the global illumination image stored by the user. In the present embodiment, the curvature circuitry 24 obtains lighting values at a plurality of locations in the image using a method similar to that described above with reference to stage 46 of FIG. 4. The locations are points on at least one surface in the image. In other embodiments, any method of analyzing the global illumination image to obtain lighting information may be used.

At stage 86, the curvature circuitry 24 uses the curvature values obtained at stage 82 and the lighting values obtained at stage 84 to relate lighting value to curvature value. For each value of curvature, the curvature circuitry 24 finds the lighting values that correspond to that curvature value. For example, a particular curvature value may occur several times in the image, and the curvature circuitry 24 may find the lighting values for all of the points at which that curvature value occurs.

In the present embodiment, the curvature circuitry 24 accumulates a 2D array of histograms with curvature in x, y and the lighting condition selection stored in the histogram. For each curvature value (k1, k2), the curvature circuitry 24 generates a histogram of lighting values that correspond to that curvature value in the image.

At stage 88, the curvature circuitry 24 returns to stage 80 if there are further GI images to be considered. At stage 80, the curvature circuitry 24 receives a further GI image. At stage 82, the curvature circuitry 24 generates a curvature image from the further GI image, which comprises determining curvature values for a plurality of locations in the further image. At stage 84 the curvature circuitry 24 analyses the lighting conditions in the further GI image, which comprises determining lighting values for a plurality of locations in the further GI image. At stage 86, the curvature circuitry 24 adds lighting values from the further GI image to the 2D array of histograms.

Stages 80 to 88 are repeated until all GI images have been analyzed and the 2D array of histograms includes lighting values from all of the GI images.

At stage 90 the curvature circuitry 24 generates a 2D transfer function based on the accumulated mapping of all the GI images. In the present embodiment, the 2D transfer function comprises a desired lighting value corresponding to each curvature value (k1, k2). In the present embodiment, the desired lighting value for a curvature value is obtained by taking an average of the lighting values that were included in the histogram for that curvature value. In other embodiments, any suitable method may be used to obtain the desired lighting value.

In the present embodiment, the 2D transfer function comprises an importance factor for each curvature value. The importance factor is representative of the importance of that curvature value to the lighting score. The importance factor provides a weighting that is dependent on importance.

In the present embodiment, a curvature value is considered to be important if the images selected by the user have a narrow spread of lighting values, indicating that the user's preference for lighting value for that curvature is very consistent. The importance factor for a curvature value may be determined in dependence on a standard deviation of lighting values in the histogram for that curvature value.

The importance factor is reduced for curvature values for which the mapping in different images disagrees. If there is a wide spread of lighting values for a particular curvature value, that curvature value is given a lower importance factor. Some areas may have a uniformly low contribution to the lighting score given their (k1, k2).

The 2D transfer function may be used to perform the method of FIG. 4 and/or FIG. 7.

The method of FIG. 8 may be used on GI images with light directions that have been manually selected by multiple different users, in order to obtain a 2D transfer function that may be considered to be generally applicable. A curvature transfer function can be generated from the users' preference by looking for light conditions that are preferred by the users at certain surface curvature values.

Alternatively, the method of FIG. 8 may be used on GI images with light directions that have all been manually selected by the same user, in order to obtain a 2D transfer function that captures the preferences of that user. The method of FIG. 8 may be used to tailor the method of FIG. 4 and/or FIG. 7 to each user.

In a case where a user selects a manual light position, the algorithm (for example, the 2D transfer function) may be extended to learn what the user likes. In some embodiments, the curvature circuitry 24 records all of the light directions (and/or other light configurations) that are manually selected by a given user, and over time creates a 2D transfer function and/or lighting scoring method that is tailored to that user. In some embodiments, the curvature circuitry 24 records the choices that the user has made when presented with multiple light directions, and uses those choices to create a 2D transfer function and/or lighting scoring method that is tailored to that user.

In some embodiments, the user specifically chooses to create a new curvature transfer function, and provides images to the curvature circuitry 24 for that purpose. The user may select images that they think best represent their preferred lighting conditions. In other embodiments, the curvature circuitry 24 may passively capture images that are selected by the user, and use those images to obtain or improve a curvature transfer function without such an action being specifically requested by the user.

The method of FIG. 8 uses a histogram approach to generate a curvature transfer function. In other embodiments, the generation of the curvature transfer function may use machine learning instead of or in addition to a histogram approach. The machine learning may be trained on images selected by a user and/or images for which the user has manually selected a lighting configuration (for example, one or more light directions).

Some embodiments above are described in relation to the fetus and in particular the fetal face. However, it is a feature of the methods described above that they may be used for any 3D or 4D medical imaging application.

In some embodiments, the methods of FIG. 4, FIG. 7 and/or FIG. 8 are used in imaging of the heart. In heart imaging, it may be desirable to have the maximum possible contrast between the valves and the background. The 2D transfer function (or other mapping function) may be configured to favor such maximum contrast. In some circumstances, a light direction may move with the heartbeat. The method of FIG. 7 may be used to provide continuity of movement.

In some embodiments, the methods of FIG. 4, FIG. 7 and/or FIG. 8 are used in imaging of osteoporosis, for example CT imaging of osteoporosis. In imaging osteoporosis, it may be important to be able to see pitting of the bone. The 2D transfer function (or other mapping function) may be configured for maximum visibility of pitting.

In some embodiments, the methods of FIG. 4, FIG. 7 and/or FIG. 8 are used in non-obstetric ultrasound imaging, for example imaging of the bladder, gallstones or other cavities.

In some embodiments, the methods of FIG. 4, FIG. 7 and/or FIG. 8 are used in CT colonoscopy or endoscopy imaging. In some such imaging, a light may be placed on or near a camera position.

In some embodiments, the methods of FIG. 4, FIG. 7 and/or FIG. 8 are used in digital forensics, for example to find stab wounds.

Methods described above may be used for any suitable modality and/or anatomy. Methods described above may be used for any appropriate 3D or 4D rendering method, which in some embodiments may not comprise global illumination.

Methods described above may be used for images rendered in any suitable projection, for example a normal projection, a fisheye projection or an unfolded projection. Curvature may be independent of the view projection, which may allow the same curvature-based lighting method to be used for different projections.

Certain embodiments provide a medical imaging method comprising a global illumination method, a light direction/location, and a lighting quality score, in which the lighting quality score is created by having surface curvature mapped into expected levels of illumination and compared against the simulated illumination for a given light direction.

Multiple light directions/locations may be tested in order to find the light direction/location with the best score.

The light direction selection may be automated for each frame of a temporal scan. The angle between the current light direction and the light direction chosen for the last frame may be used to create temporal stability in the score.

Segmentation may be used to exclude unimportant areas from the score.

The curvature transfer function may be accumulated from the user's preference by analyzing how the user manually chooses good images for captures.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus comprising processing circuitry configured to:
   obtain a medical imaging data set representative of at least part of at least one surface;
   render from the medical imaging data set at least one image of the at least part of the at least one surface, wherein the at least one image is rendered using a respective lighting configuration; and
   determine a measure of lighting quality for the at least one rendered image by, for the at least one rendered image, (1) determining, for each of a plurality of locations on the at least part of the at least one surface, a correspondence between a curvature of the at least one surface at the respective location and a lighting value at the respective location obtained from the rendering of the at least one image, wherein the each correspondence is determined by (1a) determining, based on the curvature at the respective location, a desired lighting value for the respective location and (1b) comparing the desired lighting value for the respective location and the lighting value for the respective location; and (2) calculating the measure of lighting quality based on the determined correspondences.

2. An apparatus according to claim 1, wherein the at least one image comprises a plurality of images, and the rendering of the at least one image comprises rendering each of the plurality of images using a different lighting configuration.

3. An apparatus according to claim 2, wherein each of the different lighting configurations comprises a different light position and/or direction.

4. An apparatus according to claim 2, wherein the processing circuitry is further configured to select at least one of the plurality of medical images based on the determined measures of lighting quality.

5. An apparatus according to claim 3 wherein the processing circuitry is further configured to select at least one light position and/or direction based on the determined measures of lighting quality.

6. An apparatus according to claim 1, wherein the rendering of the at least one image is performed using global illumination.

7. An apparatus according to claim 1, wherein the determining of the desired lighting value for each location comprises mapping the curvature at each location to the desired lighting value using at least one of a transfer function, a look-up table.

8. An apparatus according to claim 1, wherein the processing circuitry is further configured to perform a segmentation of the medical image data set to obtain at least one segmented region; and
   wherein the determining of the measure of lighting quality is dependent on the segmentation.

9. An apparatus according to claim 8 wherein, for each image, the plurality of locations are located within a selected at least one of the segmented regions of the medical image data set.

10. An apparatus according to claim 1, wherein the at least one surface comprises at least one surface of at least one anatomical feature of a subject.

11. An apparatus according to claim 10, wherein the at least one anatomical feature comprises at least part of at least one of: a fetus, a heart, a vessel, a bladder, a gallbladder, a colon, an organ, a tumor, and a bone.

12. A medical image processing apparatus comprising processing circuitry configured to:
   obtain a sequence of medical imaging data sets, each representative of at least part of at least one surface; and
   for each of the sequence of medical imaging data sets:
      render from the each medical imaging data set at least one image of the at least part of the at least one surface, wherein the at least one image is rendered using a respective lighting configuration; and
      determine a measure of lighting quality for the at least one rendered image by, for the at least one rendered image, (1) determining, for each of a plurality of locations on the at least part of the at least one surface, a correspondence between a curvature of the at least one surface at the respective location and a lighting value at the respective location obtained from the rendering of the at least one image, wherein the each correspondence is determined by (1a) determining, based on the curvature at the respective location, a desired lighting value for the respective location and (1b) comparing the desired lighting value for the respective location and the lighting value for the respective location; and (2) calculating the measure of lighting quality based on the determined correspondences; and wherein the measure of lighting quality is dependent on a comparison of a lighting configuration with which the medical image data set is rendered and at least one lighting configuration with which at least one preceding medical image data set in the sequence is rendered, such that more similar lighting configurations result in a better measure of lighting quality.

13. An apparatus according to claim 12, wherein the measure of lighting quality is dependent on an angle between a light direction in the medical imaging data set and a light direction in the at least one preceding medical image data set.

14. A method comprising:

obtaining a medical imaging data set representative of at least part of at least one surface;

rendering from the medical imaging data set at least one image of the at least part of the at least one surface, wherein the at least one image is rendered using a respective lighting configuration; and determining a measure of lighting quality for the at least one rendered image by, for the at least one rendered image, (1) determining, for each of a plurality of locations on the at least part of the at least one surface, a correspondence between a curvature of the at least one surface at the respective location and a lighting value at the respective location obtained from the rendering of the at least one image, wherein the each correspondence is determined by (1a) determining, based on the curvature at the respective location, a desired lighting value for the respective location and (1b) comparing the desired lighting value for the respective location and the lighting value for the respective location; and (2) calculating the measure of lighting quality based on the determined correspondences.

15. A computer program product comprising a non-transitory storage medium storage instructions that are executable to perform a method according to claim 14.

* * * * *